United States Patent
Mitra et al.

(10) Patent No.: US 7,311,896 B2
(45) Date of Patent: Dec. 25, 2007

(54) NATURAL SUNSCREEN COMPOSITIONS AND PROCESSES FOR PRODUCING THE SAME

(75) Inventors: Shankar Kumar Mitra, Karnataka (IN); Uddagiri Venkanna Babu, Karnataka (IN); Marikunte Venkata Ranganna, Karnataka (IN)

(73) Assignee: MMI Corporation (KY)

( * ) Notice: Subject to any disclaimer, the term of this patent is extended or adjusted under 35 U.S.C. 154(b) by 856 days.

(21) Appl. No.: 10/772,914

(22) Filed: Feb. 5, 2004

(65) Prior Publication Data

US 2005/0175557 A1 Aug. 11, 2005

(51) Int. Cl.
*A61Q 17/04* (2006.01)
*A61Q 19/00* (2006.01)
*A61K 36/00* (2006.01)
*A61K 8/02* (2006.01)

(52) U.S. Cl. .......................... 424/59; 424/60; 424/400; 424/401; 424/725

(58) Field of Classification Search .................. 424/59, 424/60, 400, 401, 725
See application file for complete search history.

(56) References Cited

U.S. PATENT DOCUMENTS

| | | |
|---|---|---|
| 5,756,099 A | 5/1998 | Simpson et al. |
| 5,773,014 A | 6/1998 | Perrier et al. |
| 6,440,402 B1 | 8/2002 | Gonzalez et al. |
| 6,500,869 B1 | 12/2002 | Driller et al. |
| 6,537,529 B1 | 3/2003 | Bonda et al. |

*Primary Examiner*—Shelley A. Dodson
(74) *Attorney, Agent, or Firm*—Knobbe, Martens, Olson & Bear, LLP

(57) ABSTRACT

Disclosed is a natural sunscreen composition comprising extracts of *Hedychium spicatum* and/or *Alpinia galanga* containing active sunscreen agents, the sunscreen composition devised to protect the skin from the harmful effects of short wavelength UV B rays and long wavelength UV A rays.

15 Claims, No Drawings

NATURAL SUNSCREEN COMPOSITIONS AND PROCESSES FOR PRODUCING THE SAME

BACKGROUND OF THE INVENTION

1. Field of the Invention

This invention, in general, relates to cosmetic compositions. More specifically, this invention relates to natural sunscreen compositions and processes for producing the same.

2. Description of the Related Art

Human skin is sensitive to solar rays and overexposure to sun can cause not only simple sunburn or an erythema, but also burns of varying severity. The other negative effects of over-exposure to solar rays are, tanning, immune suppression, photosensitivity or drug related photosensitivity and photo allergies. Sun can also cause the skin to lose its elasticity and form wrinkles, leading to premature ageing. Dermatosis may also be caused due to over-exposure to solar rays. In extreme cases, some people can develop skin cancer.

Outdoor activities including typical field-related jobs and sporting activities expose the skin to sun. It has been estimated that nearly 75 percent of the sun-inflicted skin damage on the average person's skin over a lifetime is the result of being just outdoors. Hence we require a protection so that we can expose ourselves to the sunlight without getting harmed. These concerns have been heightened by evidence that the earth's ozone layer has suffered severe depletion in recent years. Ozone is recognized as the stratospheric component shielding against the harmful forms of ultraviolet radiation. But still 5% of the sunrays coming to the earth are composed of the ultraviolet rays. These ultraviolet rays are composed of the shorter-wavelength (290-320 nm) UVB rays that cause indirect sun tanning and the longer-wavelength (320-400 nm) UVA rays that are responsible for direct sun tanning. Sunscreen compositions offer a scientific solution to the above-identified harmful effects of over-exposure to the ultraviolet rays.

Topical application sunscreen formulations are known. Sunscreen active are generally classified as organic sun screeners or inorganic sun screeners. Organic sun screeners absorb strongly at specific wavelengths and are transparent to visible light. However, some organic sun screeners such as Oxybenzone are known to cause photo allergic reactions. Inorganic sun screeners such as Titanium dioxide at higher levels leave visible residue referred as whitening of the skin.

To overcome these allergic side effects of organic sun screeners and non-aesthetics of inorganic sun screeners, there exist the need for devising newer formulations, that can protect the skin from the harmful effects of the ultraviolet radiations of sun without any undesirable side effects. It is against this background the present invention has been brought out.

U.S. Pat. No. 6,500,869 to Driller et al. discloses a sun protection formulation in solid or liquid form containing organic or inorganic sunscreen filters for a prophylactic action. Disclosed in this patent are substances of cinnamic acid derivatives, in particular octyl p-methoxycinnamate that function not only as light protection filters, but also as solvents for other UV filters and are therefore often used in combination with various filters.

U.S. Pat. No. 6,537,529 to Bonda et al. discloses a method of preparing a sunscreen including a solvent system and a filter system, as well as sunscreen compositions and compounds for producing sunscreen compositions.

U.S. Pat. No. 5,773,014 to Perrier et al. discloses a composition to inhibit the formation of unwanted skin pigmentation. The active components of the composition include extracts of selected plants, namely, mulberry, saxifrage, grape and scutellaria root; and, preferably, ethylene diamine tetra acetic acid (EDTA).

U.S. Pat. No. 6,440,402 to Gonzalez et al. discloses the synergistic action of *Kaempferia galanga* root extract in sunscreen formulation. The invention also discloses a method comprising introducing into the composition an amount of extract of *Kaempferia galanga* plant sufficient to enhance the photostability of the sunscreen active.

U.S. Pat. No. 5,756,099 to Simpson et al. discloses a process of preparing natural, organic, topical tanning sunscreen compositions comprising extracting the embryonic, spongy mass of tissue of the coconut from the drupe and adding it to the flesh of papaya in a proportional ratio of 1:3.

Sunscreen compositions comprising herbal extracts that can act as antioxidants are known in prior art. Sunscreen compositions containing herbal extracts such as green tea, aloe vera, calendula, chamomile rosemary are also known in the art. Further, it is known in the art to devise sunscreen compositions having cinnamic acid esters, wherein the cinnamic acid esters act as sunscreen actives. The present invention is distinct from the above prior art compositions as described hereunder.

SUMMARY OF THE INVENTION

In one preferred embodiment, there is provided a safe and effective natural sunscreen composition comprising extract of plant *Hedychium spicatum* and plant *Alpinia galanga* and a cosmetically acceptable carrier.

In another preferred embodiment, there is provided a safe and effective natural sunscreen composition comprising extract of plant *Hedychium spicatum* or plant *Alpinia galanga* and a cosmetically acceptable carrier.

In yet another preferred embodiment, there is provided a safe and effective natural sunscreen composition comprising cinnamic acid esters, individually or mixtures thereof, isolated and characterized from the extract of plant *Hedychium spicatum* and a cosmetically acceptable carrier.

In still another preferred embodiment, there is provided a safe and effective natural sunscreen composition comprising cinnamic acid esters, individually or mixtures thereof, isolated and characterized from the extract of plant *Alpinia galanga* and a cosmetically acceptable carrier.

In one another preferred embodiment, the present invention provides for a safe and effective natural sunscreen composition, wherein the composition comprises *Hedychium spicatum* extract (0.001% to 20%), Glyceryl mono stearate (0.55%), Cetyl alcohol (0.80%), Cetostearyl alcohol (0.50%), Heavy liquid paraffin (2.80%), Silicone oil (1.00%), Sorbitan stearate (0.68%), Isostearic acid (2.20%), Polysorbate 60 (0.50%), Acrylates copolymer (3.50%), Sodium hydroxide (0.14%), Glycerin (3.00%), Titanium dioxide (0.55%), Methyl paraben (0.20%) and Propyl paraben (0.10%) and demineralized water.

In a preferred embodiment, the present invention provides for a safe and effective natural sunscreen composition, wherein the composition comprises *Alpinia galanga* extract (0.001% to 20%), Glyceryl mono stearate (0.55%), Cetyl alcohol (0.80%), Cetostearyl alcohol (0.50%), Heavy liquid paraffin (2.80%), Silicone oil (1.00%), Sorbitan stearate (0.68%), Isostearic acid (2.20%), Polysorbate 60 (0.50%), Acrylates copolymer (3.50%), Sodium hydroxide (0.14%), Glycerin (3.00%), Titanium dioxide (0.55%), Methyl paraben (0.20%), Propyl paraben (0.10%), and demineralized water.

In still another preferred embodiment, the present invention provides for a safe and effective natural sunscreen composition, wherein the composition comprises cinnamic acid esters (0.001% to 8%), Glyceryl mono stearate (0.55%), Cetyl alcohol (0.80%), Cetostearyl alcohol (0.50%), Heavy liquid paraffin (2.80%), Silicone oil (1.00%), Sorbitan stearate (0.68%), Isostearic acid (2.20%), Polysorbate 60 (0.50%), Acrylates copolymer (3.50%), Sodium hydroxide (0.14%), Glycerin (3.00%), Titanium dioxide (0.55%), Methyl paraben (0.20%) and Propyl paraben (0.10%), and demineralized water.

In yet another preferred embodiment, the present invention provides for a safe and effective natural sunscreen composition, wherein the composition comprises cinnamic acid esters (0.001% to 12%), Glyceryl mono stearate (0.55%), Cetyl alcohol (0.80%), Cetostearyl alcohol (0.50%), Heavy liquid paraffin (2.80%), Silicone oil (1.00%), Sorbitan stearate (0.68%), Isostearic acid (2.20%), Polysorbate 60 (0.50%), Acrylates copolymer (3.50%), Sodium hydroxide (0.14%), Glycerin (3.00%), Titanium dioxide (0.55%), Methyl paraben (0.20%) and Propyl paraben (0.10%), and demineralized water.

In yet another preferred embodiment, the present invention provides for a safe and effective natural sunscreen composition, wherein the composition comprises cinnamic acid esters (0.001% to 8%), Glyceryl mono stearate (0.250%), Stearic acid (6.50%), Light liquid paraffin (5.50%), Isopropyl myristate (1.50%), Cetyl alcohol (1.20%), Cresmer 1000 (0.80%), Cetostearyl alcohol (1.20%), Brij 36 (0.60%), Methyl paraben (0.20%), Propyl paraben (0.10%), Glycerin (5.00%), Triethanol amine (0.80%), Fragrance (qs) and DM Water (qs to 100).

In yet another preferred embodiment, the present invention provides for a safe and effective natural sunscreen composition, wherein the composition comprises cinnamic acid esters (0.001% to 8%), Sodium lauryl ether sulphate (40%), Cocodiethanolamide (1.00%), Betaine (5.00%), Sodium chloride (1.00%), Silicone emulsion (0.50%), Methyl paraben (0.20%), Propyl paraben (0.10%), Fragrance (qs), Colour (qs) and DM Water (qs to 100).

In yet another preferred embodiment, the present invention provides for a safe and effective natural sunscreen composition, wherein the composition comprises cinnamic acid esters (0.001% to 8%), Sodium lauryl ether sulphate (35.00%), Carbomer (1.20%), Betaine (5.00%), Triethanol amine (0.80%), Silicone emulsion (0.50%), Glycerin (5.00%), Methyl paraben (0.20%), Propyl paraben (0.10%), Fragrance (qs) and DM Water (qs to 100).

It is an aspect of the present invention to provide for a method of producing a natural sunscreen composition, the method comprising extracting plant extracts from *Hedychium spicatum* by percolation, filtering the plant extract, concentrating the plant extract to dryness on a rotatory evaporator under vacuum at optimum temperature and producing a natural sunscreen composition employing the said dried mass and a cosmetically acceptable carrier.

In still another aspect, the present invention provides for a method for producing a natural sunscreen composition, the method comprising extracting plant extracts from *Hedychium spicatum* by hot-soxhalation, filtering the plant extract, concentrating the plant extract to dryness on a rotatory evaporator under vacuum at optimum temperature and producing a natural sunscreen composition employing the said dried mass and a cosmetically acceptable carrier.

It is an aspect of the present invention to provide for a method for producing a natural sunscreen composition, the method comprising extracting plant extracts from *Alpinia galanga* by percolation, filtering the plant extract, concentrating the plant extract to dryness on a rotatory evaporator under vacuum at optimum temperature and producing a natural sunscreen composition employing the said dried mass and a cosmetically acceptable carrier.

In still another aspect, the invention provides for a method for producing a natural sunscreen composition, the method comprising extracting plant extracts from *Alpinia galanga* by hot-soxhalation, filtering the plant extract, concentrating the plant extract to dryness on a rotatory evaporator under vacuum at optimum temperature and producing a natural sunscreen composition employing the said dried mass and a cosmetically acceptable carrier.

In yet another aspect, the invention provides for a method for producing a natural sunscreen composition, the method comprising extracting extracts of plant *Hedychium spicatum* or *Alpinia galanga* by percolation or hot-soxhalation, filtering the plant extract, purifying the extract by crystallization to obtain pure cinnamic acid esters and producing a natural sunscreen composition employing the pure cinnamic acid esters thus obtained and a cosmetically acceptable carrier.

In yet another aspect, the invention provides for a method for producing a natural sunscreen composition, the method comprising extracting plant extracts from *Hedychium spicatum* or *Alpinia galanga* by solvent extraction using an organic solvent selected from the group comprising petroleum ether, hexane, cyclohexane, benzene, dichloromethane, chloroform, ethyl acetate, acetone, methanol and ethanol, either alone or in combination thereof, purifying the resultant extract; separating the pure compound; characterizing the compound as cinnamic acid esters and producing the natural sunscreen composition using the cinnamic acid esters thus produced and a cosmetically acceptable carrier.

In yet another preferred embodiment, the present invention provides for a delivery system containing a natural sunscreen composition comprising extract of plant *Hedychium spicatum* and plant *Alpinia galanga* and a cosmetically acceptable carrier.

In still another preferred embodiment, the present invention provides for a delivery system containing a natural sunscreen composition comprising extract of plant *Hedychium spicatum* and plant *Alpinia galanga* and a cosmetically acceptable carrier wherein the delivery system includes creams, shampoos, gels, lotions, soaps, oils, sticks or sprays.

DETAILED DESCRIPTION OF THE PREFERRED EMBODIMENT

The invention involves identification and selection of the herbs and obtaining the extract by subjecting the same to solvent extraction. *Hedychium spicatum*, a perennial rhizomatous herb is widely found in western and eastern parts of Himalaya. Rhizomes possess a strong aromatic odour and bitter camphoraceous taste.

The rhizomes are stomachic, carminative, stimulant and tonic. They are used in dyspepsia. (Nadkarni, I, 608; Dastur, Useful plants, 122; Taylor & Dutt; Proc. Nat. Acad. Sci. India, 1940, 10A, 17). The dried rhizomes of commerce on steam distillation yield 4% of an essential oil and its main constituent being ethyl-p-methoxy cinnamate. The oil may be used as perfume for soaps; hair oils and face powders etc. (Taylor & Dutt, Loc. Cit; Dymock, Warden& Hooper, III, 419. Finnemore, 182; Wehner, I, 179, Chem Abstr; 1940, 3A, 6015). The presence of alkaloids, saponins and flavonoids has been reported in the rhizomes (Suchitra Kumar et al. J. Econ. Bot Phytochem, 1990, I, 13.) The ethanolic extract of dried rhizomes showed antibacterial activity. (Venkata Narayana et al. Indian Med. 1989, 1, 6; Mishra et al. Int J Pharmacogn, 1991, 29, 19).

*Alpinia galanga* is an herb, 1.8-2.4 m in height, with tuberous aromatic rootstocks, occurring throughout India and cultivated for its rhizomes. The rhizomes are considered as tonic, stomachic, carminative and stimulant, and are used as a fragrant adjunct to complex preparations and also in cough and digestive mixtures.

Fresh rhizomes of *Alpinia galanga* on steam distillation yield an essential oil (0.04%) with a peculiar strong and spicy odour. The oil contains methyl cinnamate (48%), cineol (20-30%), camphor and probably d-pipene. The oil is carminative and in moderate doses has an anti-spasmodic action on involuntary muscle tissue.

Disclosed herein is the process of extraction of herbs, the process comprising shade drying fresh rhizomes of *Hedychium spicatum* and/or *Alpinia galanga* and powdering the dried material coarsely. Each plant material is subjected to solvent extraction by percolation method. About 1 Kg of plant material is taken in separate flasks and soaked with petroleum ether, hexane, cyclo-hexane, benzene, dichloromethane, chloroform, ethyl acetate, acetone, methanol and ethanol for two days. All solvent extracts are drained out and filtered through Whatman Filter No.1 and concentrated to dryness on rotatory evaporator under vacuum at optimum temperature. The residual material is extracted further until all compounds are extracted. Alternately, the extraction is also performed by hot-soxhalation method for three times and processed as above.

The extract of the plant *Hedychium spicatum* is obtained by subjecting the rhizome thereof to a system of organic solvents from non-polar to polar solvents by percolation and hot-soxhalation methods. The solvent extraction with n-hexane under cold extraction for three days at room temperature and hot-refluxing at optimum temperature for three cycles was found to be very simple and unique process for obtaining 24.79% (highest yield of actives in comparison to other solvents used for extraction) of extract containing 60-70% of active cinnamic acid esters.

The yields of *Hedychium spicatum* extract were found to be n-Hexane (24.79%), Cyclo-hexane (21.12%), Petroleum ether (15.06%), Chloroform (24.72%), Dichloromethane (14.22%), Ethyl acetate (13.87%), Acetone (17.71%), Methanol (21.61%) and Ethyl Alcohol (18.42%).

The yields of *Alpinia galanga* extract were found to be n-Hexane (19.15%), Cyclo-hexane (18.16%), Petroleum ether (14.76%), Chloroform (21.16%), Dichloromethane (14.25%), Ethyl acetate (12.25%), Acetone (15.75%), Methanol (20.54%) and Ethyl Alcohol (17.42%).

All solvent extracts obtained as oil form are kept for crystallization at room temperature from 1 to 2 days and pure crystalline mixture thus obtained is washed with n-hexane (2 to 3 washes) and recrystallised in methanol to produce pure form of cinnamic acid esters. This method is simple, cost effective and applicable to bulk scale production.

The isolation of individual pure compounds is achieved by column chromatography over silica gel and eluted with n-hexane and ethyl acetate mixture as each pure compound was crystallized with hexane-ethyl acetate solvent system.

A crude mixture of cinnamic acid esters was analysed by HPTLC using Hexane and Ethyl acetate as mobile phase. The spots were visualized in Iodine vapour and also under UV light showing many closely related spots.

The isolation of cinnamic acid esters is achieved by column chromatography over silica gel (60-120 mesh) using hexane and ethyl acetate as eluent and 250 ml fractions are collected and pooled accordingly after performing HPTLC. All fractions are subjected to 4 semi-purified fractions. Further purification of these fractions is carried on HPLC using methanol as mobile phase over RP-18 column.

The isolated fractions were characterized by NMR and GC-MS and identified as P-methoxy cinnamic acid esters (STR#1 to STR#5), p-ethoxy cinnamic acid esters (STR#6 to STR#11) and p-hydroxy benzyl cinnamic acid esters (STR#12 and STR#13).

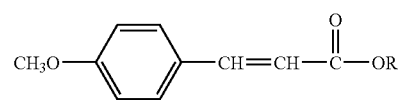

STR-01 R = Methyl
STR-02 R = Ethyl
STR-03 R = Propyl
STR-04 R = Butyl
STR-04 R = Octyl

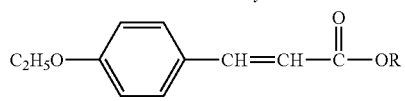

STR-06 R = Methyl
STR-07 R = Ethyl
STR-08 R = Propyl
STR-09 R = Butyl
STR-10 R = Octyl
STR-11 R = Octadecyl

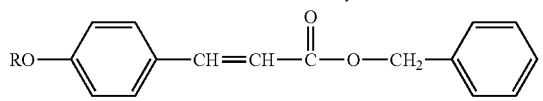

STR-12 R = Methyl
STR-13 R = Ethyl

Preferred embodiments are further illustrated in the following examples. These examples illustrate particular embodiments of the invention and are not intended to limit the scope of the invention in any way.

EXAMPLE 1

| Sl No. | Ingredients | % by weight |
|---|---|---|
| 1 | *Hedychium spicatum* extract | 0.001 to 20 |
| 2 | Glyceryl mono stearate | 0.55 |
| 3 | Cetyl alcohol | 0.80 |
| 4 | Cetostearyl alcohol | 0.50 |
| 5 | Heavy liquid paraffin | 2.80 |
| 6 | Silicone oil | 1.00 |
| 7 | Sorbitan stearate | 0.68 |
| 8 | Isostearic acid | 2.20 |
| 9 | Polysorbate 60 | 0.50 |
| 10 | Acrylates copolymer | 3.50 |
| 11 | Sodium hydroxide | 0.14 |
| 12 | Glycerin | 3.00 |
| 13 | Titanium dioxide | 0.55 |
| 14 | Methyl paraben | 0.20 |
| 15 | Propyl paraben | 0.10 |
| 16 | DM water | qs to 100 |

SPF: 13.97 Analysed by in vitro method using SPF 290S analyser

EXAMPLE 2

| Sl No. | Ingredients | % by weight |
|---|---|---|
| 1 | *Alpinia galanga* extract | 0.001 to 20 |
| 2 | Glyceryl mono stearate | 0.55 |
| 3 | Cetyl alcohol | 0.80 |
| 4 | Cetostearyl alcohol | 0.50 |
| 5 | Heavy liquid paraffin | 2.80 |
| 6 | Silicone oil | 1.00 |
| 7 | Sorbitan stearate | 0.68 |
| 8 | Isostearic acid | 2.20 |
| 9 | Polysorbate 60 | 0.50 |
| 10 | Acrylates copolymer | 3.50 |
| 11 | Sodium hydroxide | 0.14 |
| 12 | Glycerin | 3.00 |
| 13 | Titanium dioxide | 0.55 |
| 14 | Methyl paraben | 0.20 |
| 15 | Propyl paraben | 0.10 |
| 16 | DM water | qs to 100 |

SPF: 12.5 Analysed by in vitro method using SPF 290S analyser

EXAMPLE 3

| Sl No. | Ingredients | % by weight |
|---|---|---|
| 1 | A cinnamic acid esters active fraction | 0.001 to 8 |
| 2 | Glyceryl mono stearate | 0.55 |
| 3 | Cetyl alcohol | 0.80 |
| 4 | Cetostearyl alcohol | 0.50 |
| 5 | Heavy liquid paraffin | 2.80 |
| 6 | Silicone oil | 1.00 |
| 7 | Sorbitan stearate | 0.68 |
| 8 | Isostearic acid | 2.20 |
| 9 | Polysorbate 60 | 0.50 |
| 10 | Acrylates copolymer | 3.50 |
| 11 | Sodium hydroxide | 0.14 |
| 12 | Glycerin | 3.00 |
| 13 | Titanium dioxide | 0.55 |
| 14 | Methyl paraben | 0.20 |
| 15 | Propyl paraben | 0.10 |
| 16 | DM water | qs to 100 |

SPF: 19.12 Analysed by in vitro method using SPF 290S analyser

EXAMPLE 4

| Sl No. | Ingredients | % by weight |
|---|---|---|
| 1 | A cinnamic acid esters active fraction | 0.001 to 12 |
| 2 | Glyceryl mono stearate | 0.55 |
| 3 | Cetyl alcohol | 0.80 |
| 4 | Cetostearyl alcohol | 0.50 |
| 5 | Heavy liquid paraffin | 2.80 |
| 6 | Silicone oil | 1.00 |
| 7 | Sorbitan stearate | 0.68 |
| 8 | Isostearic acid | 2.20 |
| 9 | Polysorbate 60 | 0.50 |
| 10 | Acrylates copolymer | 3.50 |
| 11 | Sodium hydroxide | 0.14 |
| 12 | Glycerin | 3.00 |
| 13 | Titanium dioxide | 0.55 |
| 14 | Methyl paraben | 0.20 |
| 15 | Propyl paraben | 0.10 |
| 16 | DM water | qs to 100 |

SPF: 20.18 Analysed by in vitro method using SPF 290S analyzer

EXAMPLE 5

Sun Protection Cream

| Sl. No. | Name of Ingredients | % by weight |
|---|---|---|
| 1. | A cinnamic acid esters active fraction | 0.001 to 8 |
| 2. | Glyceryl monostearate | 0.250 |
| 3. | Stearic acid | 6.50 |
| 4. | Light liquid paraffin | 5.50 |
| 5. | Isopropyl myristate | 1.50 |
| 6. | Cetyl alcohol | 1.20 |
| 7. | Cresmer 1000 | 0.80 |
| 8. | Cetostearyl alcohol | 1.20 |
| 9. | Brii 36 | 0.60 |
| 10. | Methyl paraben | 0.20 |
| 11. | Propyl paraben | 0.10 |
| 12. | Glycerin | 5.00 |
| 13. | Triethanol amine | 0.80 |
| 14. | Fragrance | qs |
| 15. | DM Water | qs to 100 |

SPF: 19. 50 Analysed by in vitro method using SPF 290S analyser

EXAMPLE 6

Sun Protection Shampoo

| Sl. No. | Name of Ingredients | % by weight |
|---|---|---|
| 1. | A cinnamic acid esters active fraction | 0.001 to 8 |
| 2. | Sodium lauryl ether sulphate | 40 |
| 3. | Cocodiethanolamide | 1.00 |
| 4. | Betaine | 5.00 |
| 5. | Sodium chloride | 1.00 |
| 6. | Silicone emulsion | 0.50 |
| 7. | Methyl paraben | 0.20 |
| 8. | Propyl paraben | 0.10 |
| 9. | Fragrance | Qs |
| 10. | Colour | Qs |
| 11. | DM Water | Qs to 100 |

SPF: 19.20 Analysed by in vitro method using SPF 290S analyser

EXAMPLE 7

Sun Protection Gel

| Sl. No. | Name of the Ingredient | % by weight |
|---|---|---|
| 1. | A cinnamic acid ester active fraction | 0.001 to 8 |
| 2. | Sodium lauryl ether sulphate | 35.00 |
| 3. | Carbomer | 1.20 |
| 4. | Betaine | 5.00 |
| 5. | Triethanol amine | 0.80 |
| 6. | Silicone emulsion | 0.50 |
| 7. | Glycerin | 5.00 |
| 8. | Methyl paraben | 0.20 |
| 9. | Propyl paraben | 0.10 |
| 10. | Fragrance | Qs |
| 11. | DM Water | Qs to 100 |

SPF: 20.12 Analysed by in vitro method using SPF 290S analyzer

Primary Skin Irritation Test of Sun Screen Lotion in Guinea Pigs

Primary skin irritation is a localized reversible dermal response resulting from a single application of the test substance without the involvement of the immune system. The skin irritation tests are usually carried out on guinea pigs or rabbits. The study is conducted using a covered patch/open application with or with out test substance. The skin reactions are observed at 24, 48 and 72 hours. This test is designed to detect the irritancy potential of the substance under investigation.

Ten healthy Guinea pigs of Dunkin Hartley strain weighing from 425-500 g, bred in Experimental Animal Facility of R&D Center, The Himalaya Drug Company, were used for the study. The animals were randomized and divided into two groups of five each.

The animals were maintained at 22±3° C., 50-60% of humidity, 12 hours light and dark cycle, with unlimited supply of drinking water and feed. The animals were housed individually in a cage. The fur on the dorsal area of the trunk of the animals selected for the study was removed by clipping or shaving. Care was taken to avoid abrading of the skin. The remaining fur on each guinea pig's back was further removed by a depilatory cream containing thioglycollic acid and, then, the depilatory cream was washed and completely removed from the back of each of the guinea pigs. The guinea pigs were tested 24 hours after the depilatory treatment. All the guinea pigs were weighed prior to the start of test. Each guinea pig treated was immobilized in an animal holder and 0.05 ml of the test substance was applied on a portion (having a size 2×2 $cm^2$) of the back of the guinea pig. Control animals received vehicle treatment. The skin irritation was examined at 24, 48 and 72 hours after the application. The skin reactions were assessed as described below.

The assessment of skin irritation was done based on a graded scale of 0 to 4; with no erythema as 0; very slight erythema (barely perceptible) as 1; well defined erythema as 2; moderate to severe erythema as 3 and severe erythema (beet redness) to eschar formation (preventing grading of erythema) as 4.

The assessment of edema formation was done based on a graded scale of 0 to 4; with no edema as 0; Very slight edema (barely perceptible) as 1; Slight edema (edges of area well defined by definite raising) as 2; Moderate edema (raised approximately 1 mm) as 3 and Severe edema (raised more than 1 mm and extending beyond area of exposure) as 4.

Group-I animals were given vehicle treatment and served as control. Animals from Group II received single topical application of Sunscreen Screen Lotion at a dose of 0.05 ml. The dermal irritancy scores were recorded at 24, 48 and 72 hours after removal of the patch. All the values are expressed as Mean±SEM. The data were analyzed statistically using Student's t-test. The minimum level of significance was fixed at $p<0.05$.

Single application of Sunscreen Screen Lotion in guinea pigs showed no signs and symptoms of skin irritation (Table 1).

TABLE 1

Primary Skin Irritation Test of Sun Screen Lotion

| Treatment | Skin reactions | | | | | |
|---|---|---|---|---|---|---|
| | Erythema (Hours) | | | Edema (Hours) | | |
| | 24 | 48 | 72 | 24 | 48 | 72 |
| Control | 0.00 ± 0.00 | 0.00 ± 0.00 | 0.00 ± 0.00 | 0.00 ± 0.00 | 0.00 ± 0.00 | 0.00 ± 0.00 |
| Sunscreen Screen Lotion (0.05 ml/animal) | 0.00 ± 0.00 | 0.00 ± 0.00 | 0.00 ± 0.00 | 0.00 ± 0.00 | 0.00 ± 0.00 | 0.00 ± 0.00 |

TABLE 1-continued

The above findings indicate that Sun Screen Lotion is devoid of skin irritation following acute exposure to guinea pigs.

Acute Dermal Photo Irritation Test of Sun Screen Lotion in Guinea Pigs

Photoirritation test serves to indicate the existence of possible hazards likely to arise from topical application to skin of the test substance in association with exposure to light. Clinically it is characterized by skin changes showing erythema or oedema or both. Photoirritation potential may be examined by using guinea pigs.

Photoirritation test is carried out by applying the test substance topically at appropriate concentration on the skin, which is then exposed to UV light. Skin reactions are assessed at 24, 48 and 72 hours.

Albino Guinea pigs of Dunkin Hartley strain bred in Experimental Animal Facility of R&D Center, The Himalaya Drug Company, were used for the study. Five animals weighing between 450-600 g were used for the study.

The animals were maintained at 22±3° C., 50-60% of humidity, 12 hours light and dark cycle, with unlimited supply of drinking water and feed. The animals were housed individually in a cage. Sun Screen Lotion was applied topically without any dilution at a dose of 0.025 ml/animal. The fur on the dorsal area of the trunk of the animals selected for the study was removed by clipping or shaving. Care will be taken to avoid abrading of the skin. The remaining fur on each guinea pig's back was further removed by a depilatory cream containing thioglycollic acid and, then, the depilatory cream was washed and completely removed from the back of each of the guinea pigs. The guinea pigs were tested 24 hours after the depilatory treatment. Two areas of 2.5 cm×2.5 cm on the dorsal side (one in the left and other in the right) of the animal were marked using black marker. All the guinea pigs were weighed prior to the start of each test and the weights are recorded. The marked area in the left side served as irradiation irritation control site (IICS) and the right side received topical application of Sun Screen Lotion to serve as test. The rest of the surrounding area covered with a flank to serve as UV protected control. The animals are exposed to radiation 30 minutes after the application of the test substance. Prior to irradiation, the head of the animal is protected to avoid ocular effects.

The animals were kept in a top open polypropylene cage, one at a time. All the animals were irradiated with a 300 watts Wotan Ultra Vitalux lamp for 10 minutes at a distance of 25 cm (between the lamp and the dorsal aspect of the animal). Each test site was examined at 24, 48 and 72 hours after the start of the irradiation. The responses are scored blindly under a constant artificial light source according to the following grading scale and entered in the assessment record sheet.

The assessment of skin reactions following UV-irradiation were done for erythema on a graded scale of 0 to 4; with no erythema as 0; very slight erythema (barely perceptible) as 1; well defined erythema as 2; moderate to severe erythema as 3 and severe erythema (beet redness) to eschar formation (preventing grading of erythema) as 4.

The assessment of skin reactions following UV-irradiation were done for edema on a graded scale of 0 to 4; with no edema as 0; Very slight edema (barely perceptible) as 1; Slight edema (edges of area well defined by definite raising) as 2; Moderate edema (raised approximately 1 mm) as 3 and Severe edema (raised more than 1 mm and extending beyond area of exposure) as 4.

Exposure to UV-irradiation in Irradiation Irritation Control Site showed mild photo irritation at 24 and 48 hours post irradiation. UV-irradiation of animals following topical application of Sun Screen Lotion at a dose of 0.025 ml/animal showed no positive reactions of photo irritation (Table 2).

TABLE 2

Acute Dermal Photo irritation Test of Sun Screen Lotion

| Treatment | Skin reactions | | | | | |
|---|---|---|---|---|---|---|
| | Erythema (Hours) | | | Edema (Hours) | | |
| | 24 | 48 | 72 | 24 | 48 | 72 |
| Control (Irradiation Irritation Control Site) | 1.00 ± 0.45 | 1.00 ± 0.45 | 0.00 ± 0.00 | 0.00 ± 0.00 | 0.00 ± 0.00 | 0.00 ± 0.00 |
| Sun Screen Lotion (0.05 ml/animal) | 0.00 ± 0.00 | 0.00 ± 0.00 | 0.00 ± 0.00 | 0.00 ± 0.00 | 0.00 ± 0.00 | 0.00 ± 0.00 |

The above findings indicate that Sun Screen Lotion is free of photo irritation and it can be safely used in association with exposure to light.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A natural sunscreen composition comprising extract of plant *Hedychium spicatum* and/or plant *Alpinia galanga* and a cosmetically acceptable carrier.

2. The natural sunscreen composition according to claim 1, wherein the composition comprises 0.001% to 20% by weight of the extract of plant *Hedychium spicatum* and/or plant *Alpinia galanga*.

3. The natural sunscreen composition according to claim 1, wherein the cosmetically acceptable carrier comprises by weight; 0.55% of Glyceryl mono stearate, 0.80% of Cetyl alcohol, 0.50% of Cetostearyl alcohol, 2.80% of Heavy liquid paraffin, 1.00% of Silicone oil, 0.68% of Sorbitan stearate, 2.20% of Isostearic acid, 0.50% of Polysorbate 60, 3.50% of Acrylates copolymer, 0.14% of Sodium hydroxide, 3.00% of Glycerin, 0.55% of Titanium dioxide, 0.20% of Methyl paraben, 0.10% of Propyl paraben and Demineralised water.

4. A delivery system for topical application, comprising the natural sunscreen composition according to claim 1, wherein the delivery system comprises creams, shampoos, gels, lotions, soaps, oils, sticks or sprays as a vehicle for topical application of said sunscreen composition.

5. A natural sunscreen composition comprising cinnamic acid esters isolated and characterized from the extract of plant *Hedychium spicatum* and/or plant *Alpinia galanga* and a cosmetically acceptable carrier.

6. The natural sunscreen composition according to claim 5, wherein the composition comprises cinnamic acid esters individually or as mixtures thereof.

7. The natural sunscreen composition according to claim 5, wherein the composition comprises 0.001% to 12% by weight of cinnamic acid esters.

8. The natural sunscreen composition according to claim 5, wherein the cosmetically acceptable carrier comprises by weight; 0.55% of Glyceryl mono stearate, 0.80% of Cetyl alcohol, 0.50% of Cetostearyl alcohol, 2.80% of Heavy liquid paraffin, 1.00% of Silicone oil, 0.68% of Sorbitan stearate, 2.20% of Isostearic acid, 0.50% of Polysorbate 60, 3.50% of Acrylates copolymer, 0.14% of Sodium hydroxide, 3.00% of Glycerin, 0.55% of Titanium dioxide, 0.20% of Methyl paraben, 0.10% of Propyl paraben and Demineralised water.

9. A delivery system for topical application, comprising the natural sunscreen composition according to claim 5, wherein the delivery system comprises creams, shampoos, gels, lotions, soaps, oils, sticks or sprays as a vehicle for topical application of said sunscreen composition.

10. A natural sunscreen composition according to claim 5 comprising 0.001 to 8% by weight of Cinnamic acid esters and a cosmetically acceptable carrier which comprises by weight; 0.25% of Glyceryl monostearate, 6.50% of Stearic acid, 5.50% of Light liquid paraffin, 1.50% of Isopropyl myristate, 1.20% of Cetyl alcohol, 0.80% of Cresmer 1000, 1.20% of Cetostearyl alcohol, 0.60% of Brii 36, 0.20% of Methyl paraben, 0.10% of Propyl paraben, 5.00% of Glycerin, 0.80% of Triethanol amine, Fragrance and Demineralised water.

11. A delivery system for topical application, comprising the natural sunscreen composition according to claim 10 wherein the delivery system comprises creams, shampoos, gels, lotions, soaps, oils, sticks or sprays as a vehicle for topical application of said sunscreen composition.

12. A natural sunscreen composition according to claim 5 comprising 0.001 to 8% by weight of Cinnamic acid esters and a cosmetically acceptable carrier which comprises by weight; 40% of Sodium lauryl ether sulphate, 1.00% of Cocodiethanolamide, 5.00% of Betaine, 1.00% of Sodium chloride, 0.50% of Silicone emulsion, 0.20% of Methyl paraben, 0.10% of Propyl paraben, Fragrance, Colour and Demineralised water.

13. A delivery system for topical application, comprising the natural sunscreen composition according to claim 12, wherein the delivery system comprises creams, shampoos, gels, lotions, soaps, oils, sticks or sprays as a vehicle for topical application of said sunscreen composition.

14. A natural sunscreen composition according to claim 5 comprising 0.001 to 8% by weight of Cinnamic acid esters and a cosmetically acceptable carrier which comprises by weight; 35.00% of Sodium lauryl ether sulphate, 1.20% of Carbomer, 5.00% of Betaine, 0.80% of Triethanol amine, 0.50% of Silicone emulsion, 5.00% of Glycerin, 0.20% of Methyl paraben, 0.10% of Propyl paraben, Fragrance and Demineralised water.

15. A delivery system for topical application, comprising the natural sunscreen composition according to claim 14, wherein the delivery system comprises creams, shampoos, gels, lotions, soaps, oils, sticks or sprays as a vehicle for topical application of said sunscreen composition.

* * * * *

UNITED STATES PATENT AND TRADEMARK OFFICE
CERTIFICATE OF CORRECTION

| | | |
|---|---|---|
| PATENT NO. | : 7,311,896 B2 | Page 1 of 1 |
| APPLICATION NO. | : 10/772914 | |
| DATED | : December 25, 2007 | |
| INVENTOR(S) | : Shankar Kumar Mitra et al. | |

It is certified that error appears in the above-identified patent and that said Letters Patent is hereby corrected as shown below:

At column 5, line 5, delete "Pharmacogn," and insert --Pharmacol,--, therefore.

At column 6, line 23 (approx.), delete "STR-04 R" and insert --STR-05 R--, therefore.

Signed and Sealed this

Twenty-fourth Day of June, 2008

JON W. DUDAS
*Director of the United States Patent and Trademark Office*